United States Patent [19]

Avar et al.

[11] 4,324,628
[45] Apr. 13, 1982

[54] ALKYL-ARYL SULFOXIDES IN PHOTOINITIATING PROCESS AND PRODUCT

[75] Inventors: Lajos Avar, Biel-Benken; Hans-Werner Finck, Oberwil, both of Switzerland; Evelyne Kalt, Riedisheim, France

[73] Assignee: Sandoz Ltd., Basel, Switzerland

[21] Appl. No.: 212,662

[22] Filed: Dec. 3, 1980

Related U.S. Application Data

[63] Continuation-in-part of Ser. No. 49,572, Jun. 18, 1979, abandoned.

[30] Foreign Application Priority Data

Jun. 23, 1978 [CH] Switzerland .................. 6876/78
Oct. 16, 1978 [CH] Switzerland ................. 10692/78

[51] Int. Cl.$^3$ ............................................. C08F 2/50
[52] U.S. Cl. ........................ 204/159.24; 204/159.18; 204/159.19; 260/347.8; 260/351; 525/10; 525/21; 525/471; 528/128; 528/220; 549/27; 549/58; 560/11
[58] Field of Search .............. 204/159.24; 430/916, 430/921

[56] References Cited

U.S. PATENT DOCUMENTS

| | | | |
|---|---|---|---|
| 3,903,322 | 9/1975 | Ravve et al. | 204/159.24 |
| 4,054,682 | 10/1977 | Kuesters et al. | 430/921 |
| 4,111,692 | 9/1978 | Etoh et al. | 430/916 |
| 4,165,267 | 8/1979 | Avar et al. | 204/159.24 |
| 4,186,108 | 1/1980 | Carlson et al. | 204/159.24 |
| 4,198,241 | 4/1980 | Bronstert et al. | 204/159.24 |

FOREIGN PATENT DOCUMENTS

51-141622 12/1976 Japan.
1513272 6/1978 United Kingdom.

*Primary Examiner*—John C. Bleutge
*Assistant Examiner*—A. H. Koeckert
*Attorney, Agent, or Firm*—Gerald D. Sharkin; Richard E. Vila; Thomas C. Doyle

[57] ABSTRACT

The present invention relates to a photopolymerization process comprising irradiating a photopolymerizable material with U.V. light of wave length 250 to 400 nm in the presence of a photosensitizing amount of a photoinitiator of formula I,

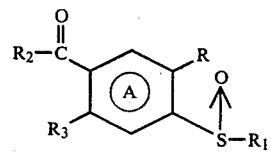

in which
R is hydrogen or halogen
$R_1$ is alkyl, cycloalkyl, benzyl, optionally substituted phenyl or (a)

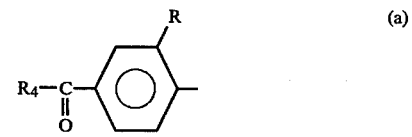

either
$R_2$ is optionally substituted alkyl, benzyl, $C_6H_5$—CH═CH—, 2-thienyl, 2-furyl, 2-(3-chloro)benzothienyl or optionally substituted phenyl, and
$R_3$ is hydrogen or $R_2$ and $R_3$ form a radical of formula (b)

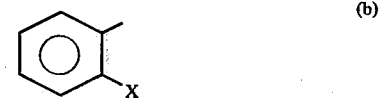

in which X is a direct bond, —O—, —S—, —CH$_2$—,

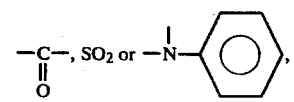

and
$R_4$ and R' have one of the significances of $R_2$ and R, respectively,
with the proviso that when $R_1$ is (a) $R_3$ is hydrogen and $R_2$ and $R_4$ are free from halogen atoms.

13 Claims, No Drawings

ALKYL-ARYL SULFOXIDES IN PHOTOINITIATING PROCESS AND PRODUCT

The present application is a continuation-in-part application of application Ser. No. 49 572 filed June 18, 1979 and now abandoned.

The present invention relates to a photopolymerization process and photopolymerizable compositions.

More particularly, the present invention provides a photopolymerization process comprising irradiating a photopolymerizable material with U.V. light of wave length 250 to 400 nm in the presence of a photosensitizing amount of a photoinitiator of formula I,

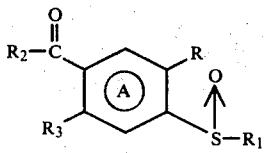

in which
R is hydrogen or halogen,
$R_1$ is $(C_{1-18})$alkyl, $(C_{5-8})$cycloalkyl, benzyl, phenyl, phenyl substituted by up to two $(C_{1-4})$alkyl groups or a group of formula (a)

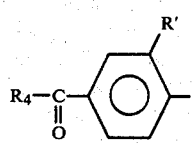

either
$R_2$ is $(C_{1-21})$alkyl; $(C_{1-21})$alkyl substituted by up to 3 halogen atoms; $(C_{1-4})$alkoxy$(C_{1-6})$ alkyl; benzyl; $(C_{1-4})$alkyl substituted by a tertiary amino group; $C_6H_5CH=CH-$, 2-thienyl, 2-furyl or 2-(3-chloro)benzothienyl; phenyl optionally substituted by up to three substituents selected from the group consisting of $(C_{1-12})$alkoxy, $(C_{1-12})$alkyl (max. 3 of each) halogen atoms (a maximum of two), hydroxy and $(C_{1-8})$alkyl ester (maximum of 1 of each of these) with the proviso that the total number of carbon atoms in all the substituents taken together is at most 12, and
$R_3$ is hydrogen,
or $R_2$ and $R_3$ together form a radical of formula (b)

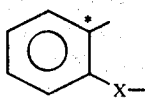

in which
X is a direct bond, $-O-$, $-S-$, $-CH_2-$,

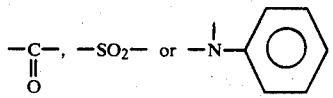

and in which the carbon atom marked with the asterisk is bound to the $>C=O$ group,
R' has one of the significances of R and
$R_4$ has one of the significances of $R_2$ except where $R_2$ and $R_3$ form a group of formula (b),
with the proviso that when $R_1$ is a group of formula (a) $R_3$ is hydrogen and $R_2$ and $R_4$ are free from halogen atoms.

Any halogen in the compounds of formula I is preferably chlorine or bromine, more preferably chlorine.

Preferably R and R' are halogen only when $R_1$ is optionally substuted phenyl or group (a). Any halogen is preferably chlorine. Preferably R and R' are the same. Most preferably both R and R' are hydrogen.

Any phenyl as $R_1$ is preferably unsubstituted or monosubstituted.

Where $R_3$ is hydrogen $R_1$ is preferably $R_1'$, where $R_1'$ is $(C_{1-18})$alkyl, benzyl, phenyl which is optionally substituted by up to two $(C_{1-4})$alkyl groups or a group of formula (a). More preferably $R_1$ is $R_1''$, where $R_1''$ is $(C_{1-12})$ alkyl, benzyl, phenyl or $(C_{1-4})$alkylphenyl or a group of formula (aa)

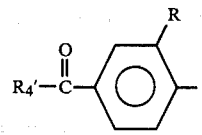

wherein $R_4'$ is defined below. Most preferably $R_1$, when $R_3$ is hydrogen, is $R_1'''$, where $R_1'''$ is $(C_{1-12})$alkyl or phenyl, particularly alkyl, with methyl, propyl, butyl, hexyl and octyl being especially preferred, most especially methyl.

Any alkyl as $R_1$ or $R_1'$, where $R_3$ is hydrogen, preferably contains 1 to 12 more preferably 1 to 8 carbon atoms.

When $R_2$ and $R_3$ form a group of formula (b) $R_1$ is preferably $R_{1X}$, where $R_{1X}$ is $(C_{1-18})$alkyl, benzyl or phenyl, more preferably $R_1$ is $R_{1X}'$, where $R_{1X}'$ is $(C_{1-18})$alkyl or phenyl. Even more preferably $R_1$ is $R_{1X}''$, where $R_{1X}''$ is $(C_{4-18})$alkyl or phenyl, with alkyl, especially $C_{4-12}$alkyl, more especially $(C_{4-8})$alkyl, being most preferred.

Any alkyl as $R_1$, $R_{1X}$ or $R_{1X}'$, when $R_2$ and $R_3$ form a group of formula (b), preferably contains 4 to 18, more preferably 4 to 12 and most preferably 4 to 8 carbon atoms.

Any alkyl as $R_2$ and/or $R_4$ which is substituted by a tertiary amine is preferably (alkyl$(C_{1-4}))_2$N-alkylene($C_{2-4}$)-,

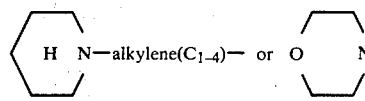

$R_2$ is preferably $R_2'$, where $R_2'$ is either $(C_{1-21})$alkyl; $(C_{1-21})$alkyl substituted by up to three halogen atoms; $(C_{1-4})$alkoxy-$(C_{1-6})$alkyl; 2-thienyl,2-furyl or 2-(3-chloro)benzothienyl; phenyl optionally substituted by up to three substituents selected from the group consisting of $(C_{1-12})$alkyl, $(C_{1-12})$alkoxy (maximum of three of each of these) halogen atoms (maximum of two thereof) and $(C_{1-8})$alkylester (maximum of one of these) with the proviso that the total number of carbon atoms in the combined substituents is at most 12 or $R_2'$ together with $R_3$ forms a group of formula (b).

More preferably $R_2$ is $R_2''$, where $R_2''$ is either $(C_{1-21})$alkyl; $(C_{1-21})$alkyl substituted by up to three halogen atoms, phenyl; phenyl substituted by a total of up to three substituents selected from $(C_{1-12})$alkyl $(C_{1-12})$alkoxy (maximum of three of each), halogen atoms (maximum of two of these) and $(C_{1-8})$alkylester (maximum of one of these) with the proviso as stated above for $R_2'$; 2-thienyl or 2-furyl or $R_2''$ with $R_3$ forms a group of formula (b). Even more preferably $R_2$ is $R_2'''$, where $R_2'''$ is either $(C_{1-12})$ alkyl, phenyl or phenyl substituted by up to two $(C_{1-9})$ alkyl groups with the proviso that the total number of carbon atoms in said combined substituents is at most 9 or $R_2'''$ with $R_3$ forms a group of formula (b) where X is $X'''$ as defined below. Yet even more preferably $R_2$ is $R_2^{iv}$, where $R_2^{iv}$ is $(C_{1-4})$alkyl, phenyl, monoalkyl$(C_{1-4})$phenyl. Most preferably $R_2$ is $R_2^v$ where $R_2^v$ is methyl, ethyl, propyl, phenyl and para-tert.butyl-phenyl with methyl or phenyl being especially preferred, particularly phenyl.

When $R_2$, $R_2'$, $R_2''$ is alkyl such alkyl preferably contains 1 to 18, more preferably 1 to 12, even more preferably 1 to 8 and most preferably 1 to 4 carbon atoms with $(C_{1-3})$alkyl, preferably methyl, being especially preferred.

When $R_2$, $R_2'$, $R_2''$ or $R_2'''$ is phenyl preferably such phenyl is unsubstituted or monosubstituted especially by an alkyl group, with unsubstituted phenyl being most preferred.

When $R_2$ or $R_2'$ is a heterocyclic group 2-thienyl and 2-furyl are preferred especially 2-furyl.

$R_3$ is preferably hydrogen.

X is preferably $X'$ where $X'$ is a direct bond, —O—, —S—, —$CH_2$— or —CO—. More preferably X is $X''$ where $X''$ is —O—, —$CH_2$—, —S— or —CO—. Most preferably X is $X'''$ where $X'''$ is O, —S— or —CO—, especially —CO— and —S—, particularly —CO—.

When $R_1$ is a group of formula (a) $R_4$ is preferably $R_4'$, more preferably $R_4''$, even more preferably $R_4'''$, yet even more preferably $R_4^{iv}$, most preferably $R_4^v$ where $R_4'$, $R_4''$, $R_4'''$, $R_4^{iv}$ and $R_4^v$ has one of the significances of $R_2'$, $R_2''$, $R_2'''$, $R_2^{iv}$ and $R_2^v$, respectively, with the exclusion of the cases where $R_2$ and $R_3$ form a group of formula (b). Most preferably $R_4$ and $R_2$ are identical with the exclusion of the case where $R_2$ and $R_3$ form a group of formula (b).

Preferred photoinitiators in the process of the present invention are those of formula I, wherein $R_1$ is $R_1'$ or $R_{1X}$, $R_2$ is $R_2'$ and when $R_1'$ is a group of formula (a) $R_4$ is $R_4'$ and when $R_2$ and $R_3$ together form a group of formula (b), X is $X'$ and any halogen as R and/or $R'$ is chlorine.

More preferred photoinitiators are those of formula Ia,

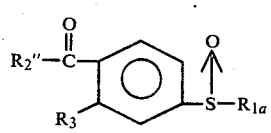

in which $R_{1a}$, when $R_3$ is hydrogen, is $R_1''$ as defined above, and when $R_3$ is part of the group of formula (b), $R_{1a}$ is $R_{1X'}$ as defined above, and X is $X'$, preferably $X''$.

Of the compounds of formula I and Ia those which are free from halogen atoms are preferred.

Most preferred photoinitiators are those of formula Ib,

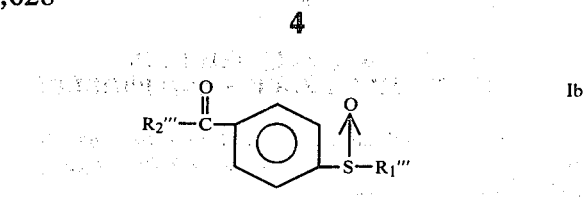

in which
$R_1'''$ is as defined above and
$R_2'''$ is as defined above except for radical (b).

The present invention further provides compounds of formula Ix,

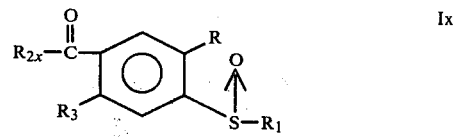

in which
$R_1$ is defined above, and when $R_1$ is a group of formula (a), as defined above, $R_4$ has one of the significances of $R_2$ as defined above and R and $R'$ are as defined above,
either
$R_{2x}$ is 2-thienyl, 2-furyl or 2-(3-chloro)benzothienyl; or phenyl optionally substituted by up to three substituents selected from the group consisting of $(C_{1-12})$alkyl $(C_{1-12})$alkoxy, (maximum of three of each) halogen atoms (a maximum of two), hydroxy and $(C_{1-8})$alkyl ester (maximum of 1 of each of these) with the proviso that the total number of carbon atoms in all the substituents taken together is at most 12, and $R_3$ is hydrogen
or
$R_{2x}$ and $R_3$ together form a group of formula (b) as defined above
with the proviso that, when X is a direct bond or —CO—, $R_1$ is other than methyl.

Preferred compounds of formula Ix, are those where $R_{2x}$ is optionally substituted phenyl or with $R_3$ forms a group of formula (b). More preferred compounds of formula Ix are those in which $R_{2x}$ is phenyl optionally substituted by up to two $(C_{1-9})$alkyl groups with the proviso that the total number of carbon atoms in the combined substituents is at most 9, or $R_{2x}$ together with $R_3$ forms a group of formula (b) where X is $X''$, $R_1$ is $R_1'$ or $R_{1X}$, preferably $R_1''$ or $R_{IX'}$, and R and $R'$ are both hydrogen. Most preferred compounds are those where $R_{2x}$ is phenyl or mono$(C_{1-4})$alkylphenyl or with $R_3$ forms a group of formula (b) where X is $X'''$, $R_1$ is $R_1'''$ and R is hydrogen, especially those where $R_3$ is hydrogen.

The present invention also provides a process for the production of compounds of formula Ix, as defined above, comprising oxidizing a compound of formula II

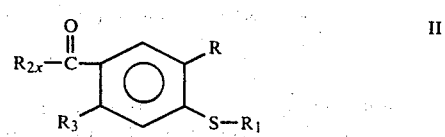

to form a sulphoxide.

The oxidation reaction may be effected in accordance with known methods. Examples of suitable oxidizing agents are H₂O₂ and meta-chloroperbenzoic acid.

The compounds of formula I which do not fall within formula Ix are either known or may be prepared in accordance with known methods from available starting materials.

The compounds of formula II may be prepared in accordance with conventional methods.

The present invention also provides photopolymerizable systems comprising a photopolymerizable substance in conjunction with a photosensitizing amount of a compound of formula I. Such photopolymerizable substances in said systems and employed in the photopolymerization process of the invention are known e.g. in the ultraviolet curable coating and printing ink arts. Preferred photopolymerizable substances are those which contain unsaturated compounds. Such systems may also contain other additives such as antioxidants, pigments and fillers. The exact amount of such substances is not critical and will vary depending on the use for which the polymerized material is designed.

One advantage of a photopolymerisable system and process of the present invention is that it is not necessary to use coinitiators such as amines which contain an α-CH-group in the process or in the system. Such amines are known in the art.

Similarly, the amount of the photoinitiator will depend on the ultimate use for which the polymerized material is designed. In general it is sufficient to employ 0.01 to 10, preferably 0.05 to 5% by weight based on the polymerizable formulation.

Finally, the present invention additionally provides a composition for effecting photopolymerization when added to a photopolymerizable material comprising a compound of formula I in admixture with an epoxidized compound. Suitable epoxidized compounds include epoxidized linseed oil. These compositions may contain up to 90% initiator.

The photopolymerization process and the photopolymerizable systems of the present invention are particularly useful in the formation of thick layers and in the formation of white pigmented systems.

The following Examples further serve to illustrate the invention. In the Examples all parts are by weight and the temperatures are in degrees Centigrade.

EXAMPLE 1

11.4 g of 4-benzoyl thioanisole are dissolved in 100 g glacial acetic acid at 10°–21°. With a little stirring the solution is reacted over a period of 15 minutes with 4.25 g of 30% H₂O₂. The mixture is then left to stand for 6 hours and subsequently poured onto 25 ml ice water. The precipitate is suction filtered, washed with water, dried and recrystallized from methanol. A white crystalline product, melting point 87° to 88° of formula

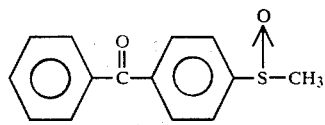

is obtained.

EXAMPLE 2

Proceeding in analogous manner to that described in Example 1 but oxidizing 4-benzoyl diphenylsulphide a white crystalline product, melting point 73° to 76° of formula

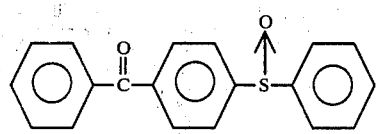

is obtained.

EXAMPLE 3

Proceeding in analogous manner to that described in Example 1 but oxidizing 4-p-tert-butyl-benzoyl diphenylsulphide a white crystalline product, melting point 144° to 146° of formula

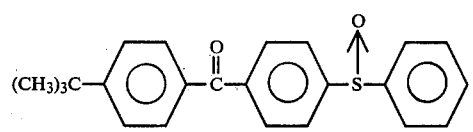

is obtained.

EXAMPLE 4

When 4-o-methylbenzoyl diphenylsulphide is oxidized, in analogous manner to the procedure described in Example 1, a resin of formula

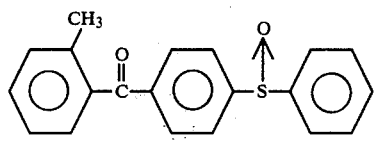

is obtained.

EXAMPLE 5

5,7 g of 2,2'-dichloro-4,4'-(tert.butyl-benzoyl) diphenylsulphide are put into 15 ml glacial acetic acid/glacial acetic acid anhydride (60:40) at 40° and are reacted with 0.85 g H₂O₂ (40%) over a period of 30 minutes, whereby a clear solution is obtained. After 4 hours stirring a further 0.85 g H₂O₂ are added and the solution is stirred for further 4 hours at the same temperature. Subsequently the solution is poured onto 200 ml ice water at 5° whereupon the reaction product precipitates. The precipitate is suction filtered, washed with water and dried. A white product, melting point 84° to 94° of formula

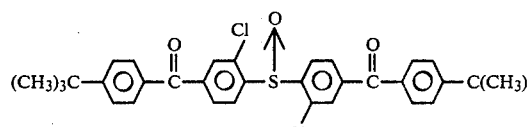

is obtained.

EXAMPLES 6–49

Proceeding in analogous manner to that described in Example 5 and oxidizing 2,2'-dichloro-4,4'-dibenzoyl diphenylsulphide a white crystalline product, melting point 114° to 117° of formula

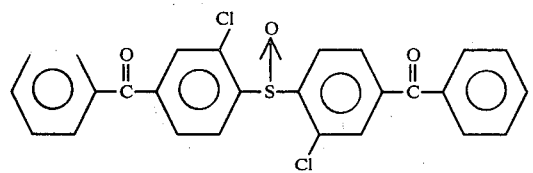

is obtained.

The compounds of the following Table 1 are prepared in analogous manner to the procedures of Examples 1 to 6.

TABLE 1

$$R_2-\overset{O}{\overset{\|}{C}}-\underset{}{\bigcirc}-\overset{O}{\overset{\uparrow}{S}}-R_1$$

| Example No. | $R_2$ | $R_1$ | m. pt. °C. |
|---|---|---|---|
| 7 | $CH_3$ | $CH_3$ | |
| 8 | $C_2H_5$ | $CH_3$ | |
| 9 | $CH_3$ | $C_8H_{17}$ | |
| 10 | $C_{11}H_{23}$ | $CH_3$ | |
| 11 | $C_8H_{17}$ | $C_8H_{17}$ | |
| 12 | | $C_8H_{17}(n)$ | ~38 |
| 13 | 2-CH₃-C₆H₄ | $CH_3$ | 102/103 |
| 14 | 4-(CH₃)₃C-C₆H₄ | $CH_3$ | 135-136 |
| 15 | 3,5-(CH₃)₂-C₆H₃ | $CH_3$ | 84-85 |
| 16 | 2-Cl-C₆H₄ | $CH_3$ | 148-149.5 |
| 17 | 4-CH₃O-C₆H₄ | $C_8H_{17}$ | |
| 18 | 4-CH₃O-C₆H₄ | $CH_3$ | 130-131 |
| 19 | 4-Cl-C₆H₄ | $CH_3$ | |
| 20 | C₆H₅ | 4-(C₆H₅CO)-C₆H₄ | |
| 21 | 4-(CH₃)₃C-C₆H₄ | 4-((CH₃)₃C)-C₆H₄-CO-C₆H₄ | |
| 22 | 2-thienyl | $CH_3$ | |
| 23 | 2-furyl | $CH_3$ | resin |
| 24 | 3-Cl-2-methyl-benzothienyl | $CH_3$ | |
| 25 | 2-COOCH₃-C₆H₄ | $CH_3$ | |
| 26 | 2-COOC₂H₅-C₆H₄ | $CH_3$ | |
| 27 | C₆H₅-CH₂- | $CH_3$ | 105 |

TABLE 1-continued $$R_2-\underset{\underset{O}{\|}}{C}-\!\!\bigcirc\!\!-\overset{\overset{O}{\uparrow}}{S}-R_1$$

| Example No. | R₂ | R₁ | m. pt. °C. |
|---|---|---|---|
| 28 | 2-OCH₃-phenyl | CH₃ | 116–117 |
| 29 | 3,4-(OCH₃)₂-phenyl | C₁₂H₂₅ | resin |
| 30 | 3,4-Cl₂-phenyl | CH₃ | 125–126 |
| 31 | 4-CH₃-phenyl | CH₃ | 135–136 |
| 32 | 3,4-(OCH₃)₂-phenyl | C₄H₉ | 79–80 |
| 33 | 3-CH₃-4-OCH₃-phenyl | CH₃ | 134–135 |
| 34 | 2-OCH₃-phenyl | C₄H₉(n) | resin |
| 35 | 3,5-di-t-C₄H₉-4-OCH₃-phenyl | CH₃ | 150–151 |
| 36 | 3,5-di-t-C₄H₉-4-OH-phenyl | CH₃ | 188–189 |
| 37 | 3,5-di-t-C₄H₉-4-OH-phenyl | CH₃ | resin |
| 38 | 2-thienyl | phenyl | 90–92 |
| 39 | 2-furyl | phenyl | 92–95 |
| 40 | 2-OH-phenyl | CH₃ | 83–84 |
| 41 | (CH₃)₃C— | CH₃ | 86.5–87 |
| 42 | (CH₃)₂CH— | CH₃ | 71–71.5 |
| 43 | phenyl | phenyl-CH₂— | 151–152 |
| 44 | 2-COOC₂H₅-phenyl | phenyl | 103.5–105 |
| 45 | phenyl | C₄H₉(n) | 82–83 |
| 46 | phenyl | —C₄H₉(t) | 57–58 |

TABLE 1-continued $$R_2-\underset{\underset{O}{\|}}{C}-\underset{}{\text{C}_6\text{H}_4}-\underset{\underset{O}{\uparrow}}{S}-R_1$$

| Example No. | R$_2$ | R$_1$ | m. pt. °C. |
|---|---|---|---|
| 47 | H$_3$C—C$_6$H$_4$— | —C$_4$H$_9$(?) | 90–92 |
| 48 | (CH$_3$)$_2$CH— | —C$_6$H$_5$ | 89–90 |
| 49 | 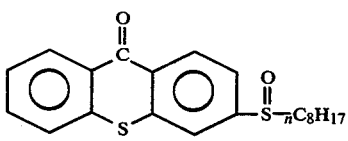 | | resin |

For example 49: C$_6$H$_5$—C(O)—C$_6$H$_3$(Cl)—S(O)—C$_4$H$_9$(n)

EXAMPLE 50

1.2 g 3-n-octylmercapto-thioxantone are dissolved in 50 ml glacial acetic acid at 50°. The solution is reacted with 0.12 ml H$_2$O$_2$ (30%) and left to stand at 50° for 20 hours. Then the solution is poured onto 100 ml ice water, whereupon the product precipitates. The precipitate is suction filtered, washed with water, dried and recrystallized from methanol. A yellow crystalline product, melting point 95° to 96° of formula

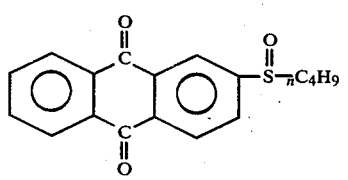

(thioxanthone with S(O)—n-C$_8$H$_{17}$)

is obtained.

EXAMPLE 51

14.2 g 2-butyl-mercapto-anthraquinone (m.pt. 117°–119°) are dissolved in 200 ml glacial acetic acid at 50°. The solution is reacted with 4.25 g H$_2$O$_2$ (30%) and stirred for 6 hours at 50°. Then a further 0.4 g H$_2$O$_2$ are added and the mixture stirred for 16 hours. The mixture is poured onto 250 ml ice water whereupon the product precipitates. The precipitate is extracted with toluene. The solution is washed neutral and the solvent is distilled off. The yellow residue is recrystallised from methanol. A yellow product, melting point 97° to 98° of formula (anthraquinone with S(O)—n-C$_4$H$_9$)

is obtained.

EXAMPLE 52

1.85 g 3-butyl-mercapto-xanthone (m.pt. 83°–84°) are dissolved in a mixture of 30 ml glacial acetic acid and 5 ml glacial acetic acid anhydride. Then the solution is reacted with 0.6 g H$_2$O$_2$ and stirred for 4½ hours at 20°. The solution is poured onto 100 ml ice water, further stirred for 15 minutes whereupon the product precipitates. The precipitate is suction filtered, washed neutral with water and dried. The product is recrystallized from methanol. A white crystalline product, melting point 128° to 130° of formula

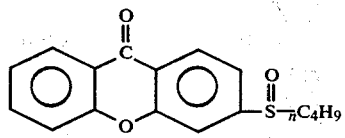

(xanthone with S(O)—n-C$_4$H$_9$)

is obtained.

The compounds of the following Table 2 are prepared in analogous manner to the procedure of Examples 50 to 52.

TABLE 2

$$\text{structure: tricyclic with C=O bridge, X bridge, and }S(O)-R_1$$

| Example No. | X | R$_1$ | m.pt. °C. |
|---|---|---|---|
| 53 | S | —C$_4$H$_9$(n) | 112–113 |
| 54 | C=O | —CH$_2$—C$_6$H$_5$ | 197–198 |
| 55 | C=O | —C$_6$H$_5$ | 174–176 |
| 56 | C=O | —C$_{12}$H$_{25}$ | 118–119 |
| 57 | C=O | —C$_{18}$H$_{37}$ | 111–120 |

APPLICATION EXAMPLE A

A mixture consisting of 70 parts EBECRYL 850 viscosity at 25° C. approximately 250 poise, mol.weight 1500 (a polyester acrylate prepolymer sold by UCB, Belgium) and 30 parts TiO$_2$ are thoroughly mixed in a roller mill. To this mixture 5% of the compound of Example 2 are added and are milled till the mixture is homogeneous. The composition is spread with a spatula in a thickness of 3 to 5μ on matt art paper and also spread on aluminium foile in a thickness of 20μ. Both films are dried in U.V. minicure apparatus (Primarc) with a mercury-medium pressure lamp (80 W/cm) at high speed until non-taky.

APPLICATION EXAMPLE B

A resin mixture consisting of 82 parts Plex 6624-0 (acrylic resin of Röhm, Darmstadt) and 18.0 parts Plex 6618-0 (acrylate based thinner, Röhm Darmstadt) and 5 parts of the compound of Example 5 are spread on matt art paper with a spatula in a thickness of 3 to 5μ. The film is dried to non-tackiness in a minicure apparatus as mentioned above in Application Example A.

APPLICATION EXAMPLE C

In analogous manner to the procedure of Example A two films, one of 3–5μ and the other of 20μ, were made employing 60 parts prepolymer of formula

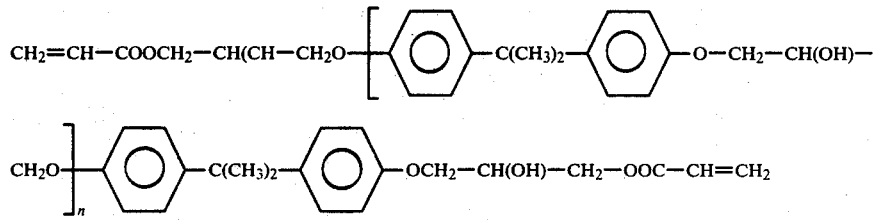

viscosity c. 9000 poise at 77° C. (see U.S. Pat. No. 3,713,864) 35 parts pentaerithriotoltetraacrylate and 40 parts $TiO_2$.

In analogous manner to the procedures described in Examples A and B and C above the compounds of Examples 1, 3, 4 and 6–57 are employed as photoinitiators.

What is claimed is:

1. A photopolymerization process comprising irradiating a photopolymerizable material with U.V. light of wave length 250 to 400 nm in the presence of a photosensitizing amount of a photoinitiator of formula I,

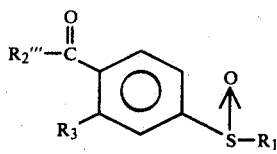

in which
$R_1$ is $(C_{1-12})$alkyl, and
either
$R_2'''$ is $(C_{1-2})$alkyl, phenyl or phenyl substituted by up to two $(C_{1-9})$alkyl groups with the proviso that the total number of carbon atoms in said combined substituents is 9,
and
$R_3$ is hydrogen,
or
$R_2'''$ and $R_3$ together form a radical of formula (b)

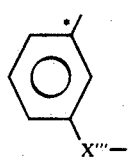

in which $X'''$ is —S— or

and in which the carbon atom marked with the asterisk is bound to the

group in formula I.

2. A process according to claim 1, in which $R_2'''$ is $(C_{1-4})$alkyl, phenyl or monoalkyl$(C_{1-4})$phenyl.

3. A process according to claim 2, in which $R_1$ is methyl, ethyl, propyl, butyl, hexyl or octyl and $R_2'''$ is methyl, ethyl, propyl, phenyl or para tert. butylphenyl.

4. A process according to claim 3, in which $R_1$ is methyl and $R_2'''$ is methyl or phenyl.

5. A process according to claim 1, in which in the compound of formula I $R_3$ is hydrogen.

6. A process according to claim 1, in which in the compound of formula I $R_3$ together with $R_2'''$ forms a radical of formula (b).

7. A photopolymerisation process according to claim 1 in which the sole photoinitiator is that of formula I.

8. A photopolymerisation process according to claim 1 in which the photoinitiator of formula I has the formula

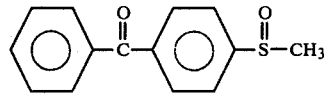

or the formula

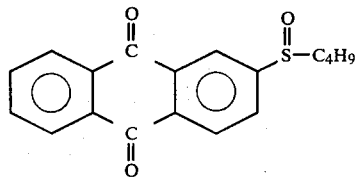

9. A photopolymerizable system comprising a photopolymerizable material in conjunction with a photosensitizing amount of a compound of formula I as defined in claim 1.

10. A photopolymerizable system according to claim 9 in which the compound of formula I is present in an amount of 0.01 to 10% by weight based on the polymerizable formulation.

11. A photopolymerisable system according to claim 9 comprising a photopolymerisable material in conjunction with a photosensitizing amount of a compound of formula I as sole photoinitiator.
12. A process according to claim 6 wherein X''' is
13. A process according to claim 2, 3, 4, 5, 6, 8, 1, or 12 wherein the amount of photoinitiator is 0.01 to 10% by weight of the photopolymerizable material.
* * * * *